United States Patent
Arsenault

(10) Patent No.: US 9,581,600 B2
(45) Date of Patent: Feb. 28, 2017

(54) IN VITRO MITOCHONDRIAL FUNCTION TEST (MFT) AND USES THEREOF

(75) Inventor: André Arsenault, Longueuil (CA)

(73) Assignee: André Arsenault, Longueuil, QC (CA)

( * ) Notice: Subject to any disclaimer, the term of this patent is extended or adjusted under 35 U.S.C. 154(b) by 0 days.

(21) Appl. No.: 13/992,407

(22) PCT Filed: Dec. 9, 2011

(86) PCT No.: PCT/CA2011/050766
§ 371 (c)(1),
(2), (4) Date: Jul. 11, 2013

(87) PCT Pub. No.: WO2012/075591
PCT Pub. Date: Jun. 14, 2012

(65) Prior Publication Data
US 2013/0280753 A1    Oct. 24, 2013

Related U.S. Application Data

(60) Provisional application No. 61/421,244, filed on Dec. 9, 2010.

(51) Int. Cl.
*G01N 33/60* (2006.01)
*G01N 33/50* (2006.01)

(52) U.S. Cl.
CPC ......... *G01N 33/60* (2013.01); *G01N 33/5076* (2013.01); *G01N 33/5079* (2013.01)

(58) Field of Classification Search
None
See application file for complete search history.

(56) References Cited

U.S. PATENT DOCUMENTS

| | | | |
|---|---|---|---|
| 5,198,670 A * | 3/1993 | VanCauter | G01T 1/204 250/328 |
| 6,183,948 B1 * | 2/2001 | Marban et al. | 435/4 |
| 7,993,859 B2 * | 8/2011 | Des Rosiers et al. | 435/7.21 |
| 2005/0169904 A1 | 8/2005 | Payne | |
| 2008/0076835 A1 * | 3/2008 | Verdin et al. | 514/789 |
| 2011/0182825 A1 | 7/2011 | Mik | |
| 2011/0312011 A1 | 12/2011 | Valla | |

FOREIGN PATENT DOCUMENTS

| WO | WO 2005/042560 A1 | 5/2005 |
|---|---|---|
| WO | WO 2010/019041 A1 | 2/2010 |
| WO | WO 2010/101950 A1 | 9/2010 |

OTHER PUBLICATIONS

Younes et al., Mechanism of uptake of technetium-tetrofosmin. Journal of Nuclear Cardiology, vol. 2:327-33, Aug. 1995.*
Cortassa et al., An Integrated Model of Cardiac Mitochondrial Energy Metabolism and Calcium Dynamics, Biophysical Journal, vol. 84, 2734-2755, Apr. 2003.*
Bazil et al., Modeling Mitochondrial Bioenergetics with Integrated Volume Dynamics, PLOS Computational Biology, Jan. 2010.*
Lanza et al., Functional Assessment fo Isolated Mitochondria In Vitro, Methods Enzymology, 2009, 457:349-372.*
Carpenter et al., Configuring Radioligand Receptor Binding Assays for HTS Using Scintillation Proximity Assay Technology, Methods in Molecular Biology, vol. 190, 2002.*
Shrikhande et al., Fully Automated Radioligand Binding Filtration Assay for Membrane-Bound Receptors, BioTechniques 33:932-937 (Oct. 2002).*
Pall, Pall Microwell filter plates catalog, 2007.*
Ross et al., Rapid and extensive uptake and activation of hydrophobic triphenylphosphonium cations within cells, Biochemical Journal, Portland Press, 2008, 411 (3), pp. 633-645.*
Logan et al., Graphical Analysis of Reversible Radioligand Binding from Time-Activity Measurements Applied to [N-11C-methyl]-(–)-Cocaine PET Studies in Human Subjects, Journal of Cerebral Blood Flow and Metabolism, 10:740-747, 1990.*
Chang YY et al., A new noninvasive test to detect mitochondrial dysfunction of skeletal muscles in progressive supranuclear palsy. Ann N Y Acad Sci. May 2005;1042:76-81.
Metivier D et al,. Cytofluorometric detection of mitochondrial alterations in early CD95/Fas/APO-1-triggered apoptosis of Jurkat T lymphoma cells. Comparison of seven mitochondrion-specific fluorochromes, Immunology Letters, vol. 61, Issues 2-3, April 1998, pp. 157-163.
PCT/CA2011/050766 international preliminary report.
PCT/CA2011/050766 international search report with related claims.
Veerkamp JH et al., An accurate and sensitive assay of [14C]octanoate oxidation and its application on tissue homogenates and fibroblasts, Biochimica et Biophysica Acta (BBA)—Lipids and Lipid Metabolism, vol. 876, Issue 1, Mar. 21, 1986, pp. 133-137.
D1: Zhang et al: "Assay of mitochondrial functions by resazurin in vitro". Acta Pharmacol Sin 25(3): 385-389, Mar. 2004.

\* cited by examiner

*Primary Examiner* — Taeyoon Kim
*Assistant Examiner* — Srikanth Patury
(74) *Attorney, Agent, or Firm* — Anglehart et al.

(57) ABSTRACT

The present document describes an in vitro method for determining a level of mitochondrial function from a subject by determining a change in a labeled compound labeling a viable cell or tissue sample isolated from a subject following introduction of a volume of a solution over said viable cell or tissue sample. The comparison of the change to a normal reference is indicative of mitochondrial function in the subject.

12 Claims, 7 Drawing Sheets

IN VITRO MITOCHONDRIAL FUNCTION TEST (MFT) AND USES THEREOF

FIELD OF THE INVENTION

The subject matter disclosed generally relates to methods of determining the mitochondrial function of a subject. More specifically, the subject matter relates to an in vitro method for determining a level of mitochondrial function in a subject by determining a change in presence of a labeled compound specific for reduction by mitochondria.

BACKGROUND OF THE INVENTION

Mitochondria are responsible for generating the energy required for cell activities from oxygen and ingested food. Accordingly, when mitochondria do not function properly, a cell's ability to make energy is reduced or stopped, and metabolic intermediates and toxic by-products begin to accumulate. The resulting energy shortage in cells and tissues can cause a number of problems including, but not limited to, muscle weakness and fatigue as well as problems in the heart, kidneys, eyes and endocrine system. The build up of toxic intermediates can be responsible for liver problems, muscle cramps, brain dysfunction or even greater mitochondrial damage. Furthermore, the build up of toxic intermediates can have a negative effect on mitochondrial energy production further impeding normal cellular metabolism and exacerbating the energy shortage.

Mitochondrial dysfunction (MD) presents a serious challenge to eukaryotic cells and associated tissues and organs. Suitable methods of determining metabolic function and more specifically mitochondrial function are therefore desirable.

Certain methods and substances for determining mitochondrial dysfunction that use label compounds have been described in the art. Fujibayashi et al. (U.S. Pat. No. 5,843,400) describe specific radioactive tracer agents for use in the diagnosis of hypoxia or mitochondrial dysfunction that are retained in regions of electron excess. Chang et al (Annals of the New York Academy of Sciences 1042: 76-81 (2005)) describe the use of the heart perfusion labeled compound 99 mTc-sestamibi with single photon emission computed tomography (SPECT) to look at mitochondrial function in the quadriceps muscles of patients with progressive supranuclear palsy.

Ayalew et al. (Journal of Nuclear Medicine 2002; 43:566-574) investigated the role of cellular metabolic disorders in influencing labeled compound uptake and modelled the concentration ratios of labeled compound in perfused isolated rabbit hearts.

Hyperaemic reactivity is a known method in the art for discriminating patients with endothelial dysfunction (ED) (See Arsenault, U.S. Pat. No. 6,445,945). The approach is based on the intravenous injection of a labeled compound such as Tc-99m-tetrofosmin (Tc-99m) and the simultaneous non-invasive external detection of the tracer ingress and transit into both forearms: one forearm submitted to reactive hyperemia and the other contralateral forearm serving as a non-hyperemic control. Patients with ED exhibit distinct time activity curves showing tracer ingress compared to patients without ED.

Although a link between ED and MD has been postulated in the art, the precise relationship between ED and MD remains a topic of speculation. Furthermore, given the complexity of the relationship between ED and MD, measures of ED by themselves would be expected to provide only an extremely crude and potentially inaccurate indication of the presence of MD.

Furthermore, the measurement of ED requires the control of vasoconstriction and vasodilation in order to modulate the blood flow (and $O_2$ flow) to the tissues in the patient himself, which may be cumbersome and more costly in terms of patient management and hospital resources.

Therefore, there is a need for method of evaluating mitochondrial function and a need for a method of evaluating mitochondrial function in vitro.

Therefore, there is a need for a method of evaluating mitochondrial function in a system (or subsystem) that is independent of the endothelial function.

SUMMARY

According to an embodiment, there is provided an in vitro method for directly determining efficiency of mitochondrial function of a subject comprising: a) subjecting viable cell or tissue sample isolated from the subject to a volume of a solution containing a labeled compound specific for reduction by mitochondria of the sample; b) washing the sample and determining a change in presence of the labeled compound to determine efficiency of mitochondria based on reduction of said labeled compound.

The method may further comprise a step of comparing the change in presence of a labeled compound to a reference to correlate to a state of mitochondrial function.

The method may further comprise comparing the change in presence of a labeled compound to a blank sample to obtain a measure of mitochondrial function in the subject.

The blank sample may be a sample having no cell or tissue. The blank sample may be a sample of viable cell or tissue whose mitochondrial activity has been blocked with a mitochondrial inhibitor molecule.

The change may be a change in an amount of said labelled compound. The decrease in the labeled compound amount may be indicative of a deficient mitochondrial function.

The increase in the labeled compound amount may be indicative of a competent or upregulated mitochondrial function.

The change in presence of a labeled compound further comprises modeling an amount of a labeled compound using quantitative dynamic modeling techniques to include at least 3 compartments, wherein one of the compartment may be indicative of mitochondrial function.

The reference may be from one of a normal subject or a diseased subject.

The compound specific for reduction by mitochondria may be selected from the group consisting of Nicotinamide adenine dinucleotide (NAD), flavin adenine dinucleotide (FAD), Flavin mononucleotide (FMN) and Ubiquinone.

The labeled compound may be labeled with a radioactive marker and a colored marker.

The colored marker may comprise at least one of a fluorescent chromophore, or a chromophore visible under visible light.

The radioactive marker may be chosen from $^{99m}$Tc-sestamibi, $^{99m}$Tc-stannous colloid, $^{99m}$Tc-hexamethyl-propylene amine oxime (HMPAO), $^{99m}$Tc-ethylenedicysteine-deoxyglucose, $^{99m}$Tc-tetrofosmin, $^{201}$Thaliumchloride, $^{62}$Cu-glyoxal bis(N4-methylthiosemicarbazone), $^{62}$Cu glyoxal bis(N4-dimethylthiosemicarbazone), $^{62}$Cu-ethylglyoxal bis(N4-methylthiosemicarbazone), $^{62}$Cu-ethylglyoxal bis(N4-ethylthiosemicarbazone), $^{62}$Cu-pyruvaldehyde bis (N4-methylthiosemicarbazone), $^{62}$Cu-pyruvaldehyde bis (N4-dimethylthiosemicarbazone), $^{62}$Cu-pyruvaldehyde bis (N4-ethylthiosemicarbazone), $^{62}$Cu-diacetyl bis(N4-methylthiosemicarbazone), $^{62}$Cu-diacetyl bis(N4-dimethylthiosemicarbazone), $^{62}$Cu-diacetyl bis(N4-ethylthiosemicarbazone), $^{62}$Cu-disalicylaldehyde-1,3-propanediamine, $^{62}$Cu-disalicylaldehyde-2,2-dimethyl-1,3-propanediamine, $^{62}$Cu-di-4-methoxysalicylaldehyde-1,3-propanediamine, $^{62}$Cu-di-4-methoxysalicylaldehyde-2,2-dimethyl-1,3-propanediamine, $^{62}$Cu-diacetylacetone ethylenediamine, and $^{62}$Cu-diacetylacetone-1,2propanediamine. The radioactive marker may be $^{99m}$Tc-tetrofosmin.

The determining a change in presence of a labeled compound may comprise measuring a light intensity of the sample before and after introduction of the volume of a solution over the sample, wherein the light intensity may be at least one of a fluorescence intensity or a visible light intensity.

The determining a change in presence of a labeled compound may comprise measuring a light intensity of the volume of a solution before and after introduction of the volume of a solution over the sample, wherein the light intensity may be at least one of a fluorescence intensity or a visible light intensity.

The determining a change in presence of a labeled compound may comprise measuring radiation emitted from the sample before and after introduction of the volume of a solution over the sample.

The determining a change in presence of a labeled compound may comprise measuring radiation emitted from the volume of a solution before and after introduction of the volume of a solution over the sample.

The volume of a solution may be collected in a collection unit. The washing may be with a saline wash, an ethanol wash, or both a saline wash and an ethanol wash.

The determining a change in presence of a labeled compound may comprise measuring radiation emitted from the saline wash, the ethanol wash, or both the saline wash and ethanol wash.

The determining may comprise a plurality of predetermined points in time following introduction of the volume of a solution over the sample. The determining may comprise at least two points in time following introduction of the volume of a solution over the sample. The determining may comprise continuously measuring points in time following introduction of the volume of a solution over the sample.

The tissue or cell sample may be selected from the group consisting of a leukocyte, a muscle tissue, a connective tissue, an epithelial tissue and a nervous tissue.

The leukocyte may be at least one of a neutrophil, an eosinophil, a basophil, a T lymphocyte, a B lymphocyte, a NK cell, a monocyte, a macrophage, and a dendritic cell.

The muscle may be at least one of a visceral muscle, a skeletal muscle and a heart muscle.

The epithelial tissue may be at least one of skin tissue, airways tissue, digestive tract tissue, and reproductive tract tissue.

The tissue or cell sample may be from a bone marrow.

According to another embodiment, there is provided a method of measuring a mitochondrial related disease comprising analyzing the level of mitochondrial function obtained according to the present invention.

The mitochondrial related disease may be at least one of an insulin resistance, a cancer, an infertility, a diabetes, a heart diseases, a blindness, a deafness, a kidney disease, a liver disease, a stroke, a migraine.

The disease may be an oxidative stress associated disease. The oxidative stress related disease may be at least one of Parkinson's disease, atherosclerosis, heart failure, myocardial infarction, a diabetes, Alzheimer's disease, schizophrenia, bipolar disorder, and chronic fatigue syndrome.

In some embodiments of the present invention, a filter that is permeable to a washing solution and a labeled compound but impermeable to a sample cell or tissue is used to isolate/separate the two compartments.

In other embodiments, one or a combination of kinetic parameters such as an initial specific labelling, a slope, a steady state value, a difference between initial specific labelling value and a steady state value, a summation of total labelling, attaining a steady state in a predetermined time are used to provide a better correlation between mitochondrial function and a disease.

According to an aspect of the present invention, there is provided a method for diagnosing a disease in a patient comprising: providing blood cells from said patient, said blood cells containing mitochondria; and measuring a level of mitochondrial activity in said blood cells using a radioactively labeled compound, said compound being reduced by said mitochondria such that said compound is retained inside said blood cell as a function of mitochondrial activity; and wherein said level of mitochondrial activity is one of a surrogate marker of said disease and an indication of a likelihood of a disease.

In some embodiments, the surrogate marker indicates an initiation, a progression and a remission of said disease or physiological mechanism involved in an initiation, a progression or a remission.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION OF THE PREFERRED EMBODIMENTS

Figure 1:
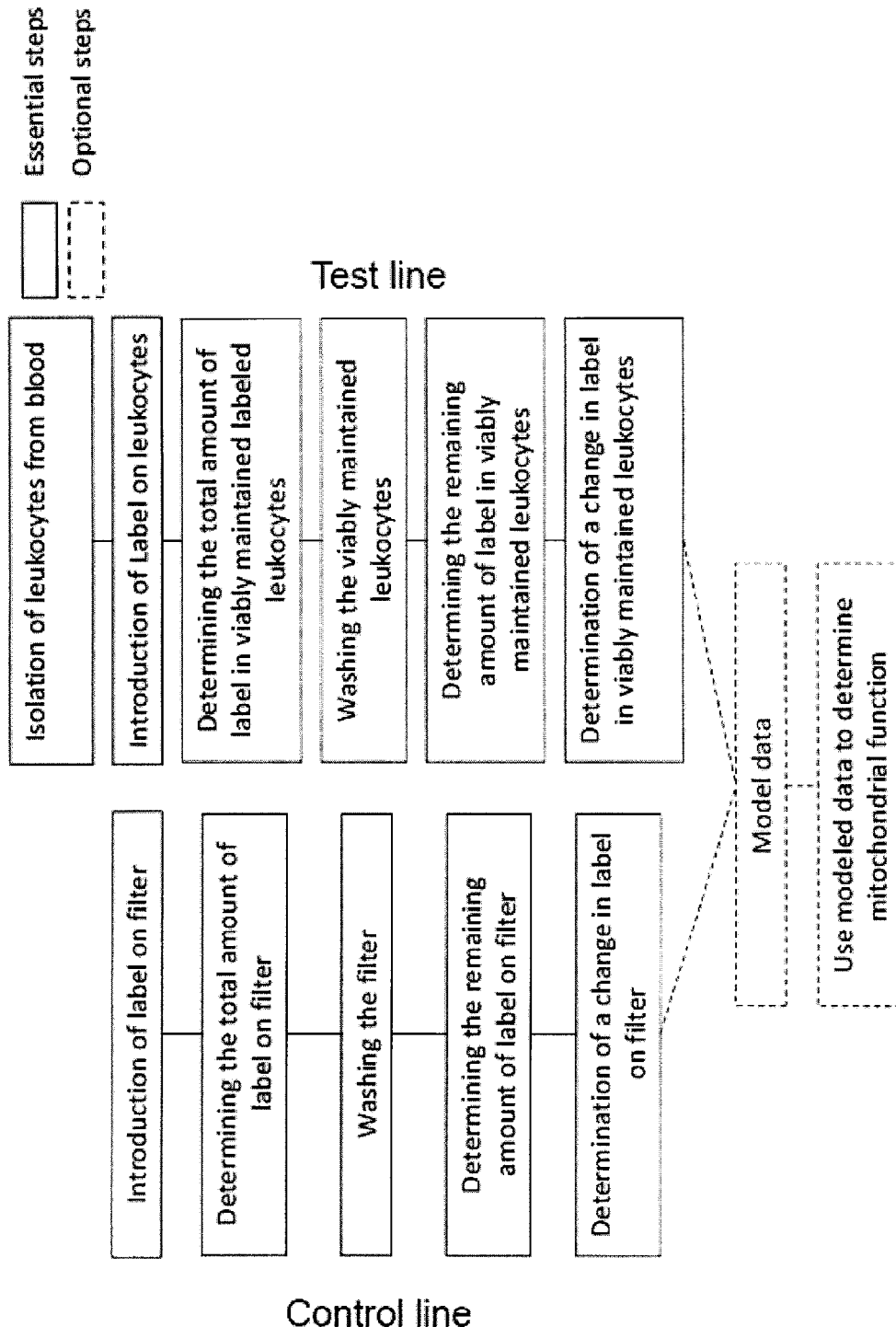
FIG. 1 illustrates a flow chart of the method according to one of the preferred embodiments.

This application relates generally to a novel in vitro method for determining a level of mitochondrial function in a subject. The method measures the capacity of cells or tissues samples to respond to stimuli that require the mitochondria. The method of the present invention measures, for example, the ratio of a retained marker by the cells of the sample in order to evaluate the efficiency of the mitochondria. According to an embodiment of the present invention, there is provided a method of measuring if the energy intake, through aerobic glycolysis, of the cells or tissues of interest is proper, and that mitochondrial dysfunction is prevented.

It will be understood by those skilled in the art that if the biological sample is a population of isolated cells (such as blood cells), separation of a marker present inside the cell from a marker outside the cell can achieved by a passing a volume of wash solution, such as saline, over the cells. When the sample is a tissue having a plurality of cells in an organized network with interstitial space, marker can be released from a cell into the interstitial space without being washed away with a wash solution. It is in the latter cases where multi-compartment models using statistics can be used to approximate the amount of labelled compound in each compartment. It will also be understood that marker, labelled compound and labelling compound are all synonymous.

In one embodiment, there is described a method for determining a level of mitochondrial function through the quantitative time/space modelling of intensity data in a sample of isolate leukocytes to contain at least 3 compartments.

In one embodiment, there is described a method for determining a level of mitochondrial function from a subject in vitro. A sample of cells (or a tissue sample), that have been isolated from a subject and labeled with a suitable labeled compound a priori are subjected to the introduction of a volume of a suitable solution. The cells may be leukocytes, white blood cells that have been isolated from the blood of a subject. Example of leukocytes include but are not limited to neutrophils, eosinophils, basophils, T lymphocytes, B lymphocytes, NK cells, monocytes, macrophages, and dendritic cells. According to another embodiment, the cells may be cells isolated from a muscle tissue, a connective tissue, an epithelial tissue and a nervous tissue. For example, muscle cells may be isolated from visceral muscles, skeletal muscle or heart muscle. According to another embodiment, the cells may be isolated from epithelial tissues, including but not limited to skin tissue, airways tissue, digestive tract tissue, and reproductive tract tissue. According to another embodiment, the cells may bone marrow cells.

The presence of the suitable labeled compound is measured in the sample and/or the volume of suitable solution and compared to a reference. The reference sample may be obtained, for example, from a normal subject, or a diseased subject, or may simply be compared to available reference values to which the measured value(s) may be compared.

In one embodiment, a measure of the labeling of the sample of cells is established and is used to estimate the competence of the mitochondria to retain the suitable labeled compound and represents by proxy the health of the mitochondria. The amount of labeled compound released into the volume of suitable solution represents the labeled compound that was not retained by the cell sample.

During measurement of the labeled compound in the test sample, a blank sample (without cells or tissue) is measured in parallel such that comparative measurement representing an "empty" sample may be collected and used appropriately in the calculations necessary to obtain the measure of mitochondrial function in the subject of interest. According to another embodiment of the present invention, a blank may be an aliquot sample of the subject's leukocytes whose mitochondrial activity has been blocked by addition of a specific mitochondrial inhibitor molecule and used appropriately in the calculations necessary to obtain the measure of mitochondrial function in the subject of interest.

The comparison is then correlated to the mitochondrial function in said subject. In one embodiment, the change is a change in the amount of the labeled compound. In one embodiment, the correlation is to a decrease in labeled compound that is indicative of a deficiency in mitochondrial function. In another embodiment, the correlation is to an increase in labeled compound that is indicative of an increase in the efficiency of mitochondrial function.

The presence of the labeled compound or tracer molecule may be measured in a static fashion, in predetermined compartments of the analytical setup after the volume of suitable solution has been introduced over the cell sample. The presence of the suitable labeled compound is measured in the cell sample, before and after introduction of a volume of solution, and in the volume of suitable solution that has been washed over the sample. The presence of the labeled compound may also be measured over time, to record rates of accumulation of the suitable labeled compound in the different compartments of an apparatus designed to carry out the analysis. The speed of the increase in accumulation of the labeled compound in the compartments may be recorded simultaneously in real time in both a test sample (the test sample of cells or tissue) and in a blank sample (comprising all the compartments, but excluding a cell sample or comprising a cell sample whose mitochondrial activity has been blocked by addition of a specific mitochondrial inhibitor molecule) The time-course data of the presence of the labeled molecule is then modeled using quantitative kinetic modeling techniques to include a component indicative of mitochondrial function. Ratios of the data test vs blank samples may be used, as appropriate. In one embodiment, the time course data is modeled into 3 or more compartments representing the volume of suitable solution uptake of the labeled compound, the uptake into the mitochondria, as well as a compartment thought to represent the presence of the labeled compound in the released fluid after passage over the cell sample. The modeled data can then be used to generate suitable metrics of mitochondrial function. In particular, it has been noted that the relative size of the compartment is related to mitochondrial dysfunction.

As used herein, a level of mitochondrial function refers to a measure of the responsiveness and capacity of a tissue or cell to function and produce energy. Mitochondrial function refers to the mitochondria's ability to generate energy in the form of ATP in response to normal cellular signaling.

As used herein, leukocytes are the cells of the immune system (white blood cells) involved in defending the body against both infectious disease and foreign materials. Five different and diverse types of leukocytes exist, but they are all produced and derived from a multipotent cell in the bone marrow known as a hematopoietic stem cell. Leukocytes are found throughout the body, including the blood and lymphatic system. According to the present inventions, the leukocytes are isolated from blood drawn from a subject and collected through sedimentation of the said sample to recover them in their live state. The leukocytes may be isolated from a routine blood draw, and subsequently labeled as known in the art for several other procedures requiring such labeling. Alternatively, the leukocytes may be isolated using automated or semi-automated leukophoresis procedures that permit isolation of leukocytes from blood while reintroducing the remaining blood cells and other components in the subject.

As used herein cells or tissue represent any type of cells present in a subject. The cells may be individual, dissociated cells or they may cells that are part of a tissue or an isolated piece of a tissue (such as a tissue biopsy) that are not dissociated into individual cells.

In one aspect of the invention, a labeled compound is used in order to determine a level of mitochondrial function. According to another embodiment of the present invention, the labeled compound is specifically reduced by the mitochondria present in the cells or tissue of the sample being analyzed. The capacity of the mitochondria to reduce the labeled compound is employed to represent the health and/or efficiency of the cells and/or tissue. The cells or tissue are labeled (or marked) with such a labeled compound, such as a radioactive marker, and/or a colored marker. In one embodiment colored markers include but are not limited to fluorescent chromophores, and/or chromophores that are visible under visible light. In another embodiment, the labeled compound may include molecules such as 99mTc-tetrofosmin (Myoview™ GE healthcare) or 99mTc-sestamibi (Cardiolite®, Bristol-Myers Squibb). In other embodiments the labeled compound is labelled with other radioactive substances or detectable markers such as 99mTc-stannous colloid, 99mTc-hexamethyl-propylene amine oxime (HMPAO), 99mTc-ethylenedicysteine-deoxyglucose, 201 Thalium-chloride, 62Cu-glyoxal bis(N4-methylthiosemicarbazone), 62Cu glyoxal bis(N4-dimethylthiosemicarbazone), 62Cu-ethylglyoxal bis(N4-methylthiosemicarbazone), 62Cu-ethylglyoxal bis(N4-ethylthiosemicarbazone), 62Cu-pyruvaldehyde bis(N4-methylthiosemicarbazone), 62Cu-pyruvaldehyde bis(N4-dimethylthiosemicarbazone), 62Cu-pyruvaldehyde bis(N4-ethylthiosemicarbazone), 62Cu-diacetyl bis(N4-methylthiosemicarbazone), 62Cu-diacetyl bis(N4-dimethylthiosemicarbazone), 62Cu-diacetyl bis(N4-ethylthiosemicarbazone), 62Cu-disalicylaldehyde-1,3-propanediamine, 62Cudisalicylaldehyde-2,2-dimethyl-1,3-propanediamine, 62Cu-di-4-methoxysalicylaldehyde-1,3-propanediamine, 62Cu-di-4-methoxysalicylaldehyde-2,2-dimethyl-1,3-propanediamine, 62Cu-diacetylacetone ethylenediamine, and 62Cu-diacetylacetone-1,2-propanediamine. The use of suitable labeled compounds incorporating the 68mCu or 82Rb isotopes is also contemplated in this application. The use of additional substances having the property of being maintained in the mitochondria by a mechanism dependent on the mitochondrial membrane potential are also contemplated in this application. Such compounds include but are not limited to Nicotinamide adenine dinucleotide (NAD), flavin adenine dinucleotide (FAD), Flavin mononucleotide (FMN) and Ubiquinone, approximately labeled.

In another embodiment of the invention, the amount of the labeled compound is measure using a detector such as a spectrophotometer and/or a fluorometer to measure the intensity of the chromophore(s) present in the leukocyte sample and/or the volume of solution over time. The change in a labeled compound can be calculated based on the light intensity of the cells or tissue sample and/or the volume of solution before and after introduction of the volume of a solution over said cells or tissue sample.

In another embodiment of the invention, the amount of labeled compound is measured using a detector or method such as scintigraphy that is able to provide multiple measurements of the concentration of the labeled compound over time in the cells or tissue sample and/or the volume of solution over time.

In a preferred embodiment, the amount of a radioactive tracer present in the region of interest is measured using a conventional gamma ray probe or a scintillation camera. Such instruments are able to provide measurements of the increasing (or decreasing) presence of a radioactive isotope exiting the cells or tissue sample (or entering the volume of solution, or both) following the introduction of a volume of solution. Other methods capable of detecting the presence of a labeled compound over time are also considered within the scope of this application.

In one embodiment, the amount of the labeled compound is measured once, and at least one additional measurement of the presence of the labeled compound is also performed. In another embodiment, the amount of labeled compound is repeatedly measured within a plurality of predetermined points in time following introduction said volume of a solution over said cells or tissue sample. In one embodiment, the amount of labeled compound is measured in the cells or tissue sample before and after the volume of a solution is introduced over said cell sample, and the amount of labeled compound is measured in the volume of solution after passage over the cells or tissue sample. In another embodiment, the volume of solution is collected in a collection unit, and the amount of labeled compound present therein is measured. In another embodiment, the volume of solution collected in a collection unit is washed with volumes of saline and/or ethanol (or both) for further fractionation into saline and ethanol fractions, which are respectively representative of the free isotope (e.g. free $^{99m}Tc$) and the free labeled compound not fixed by the mitochondria [e.g. unfixed $^{99m}Tc$tetrofosmin (Myoview™)] soluble in the washes of the volume of solution collected in the collection unit. In yet another embodiment, the eluates from the saline and ethanol washes may be further fragmented into smaller fractions as deemed appropriate by the experimental protocol and/or analytical model used.

In one embodiment of the invention, quantitative modeling of tracer kinetic data over time/space is used to provide measures of mitochondrial function. Examples of the use of quantitative modeling techniques are described in Feng D, Huang, S C and Wang X M: Models for computer simulation studies of input functions for tracer kinetic modeling with positron emission tomography. Int J Biomed Comput, 1993; 32:95-110; Timothy R. DeGrado, Steven R. Bergmann, Chin K. Ng; David M. Raffel, Tracer kinetic modeling in nuclear cardiology. J. Nucl Cardiol 2000; 7:686-700 and Muzic F. R; and. Christian T. B: Evaluation of objective functions for estimation of kinetic parameters. Am Assoc. Phys. Med. 2006 33:342-353, which are hereby incorporated by reference.

Generally, tracer kinetic modeling requires the measurements of the tracer time activity curves in both a volume of solution and in the cells or tissue sample to estimate the physiological parameters, i.e. to fit the parameters of certain compartment models as the model input and output functions, respectively. However, activity time curves measured using scintigraphy represent the cross-contamination of the true cell or tissue sample activity, and the volume of fluid.

Scintigraphy cannot support the complex modeling analysis to distinguish these components because it lacks absolute quantification of radioactivity concentration (planar imaging) or has insufficient temporal resolution (See for example, Feng et al. *Models for computer simulation studies of input functions for tracer kinetic modeling with positron emission tomography.* Int J Biomed Comput, 1993; 32:95-110).

Figure 2:
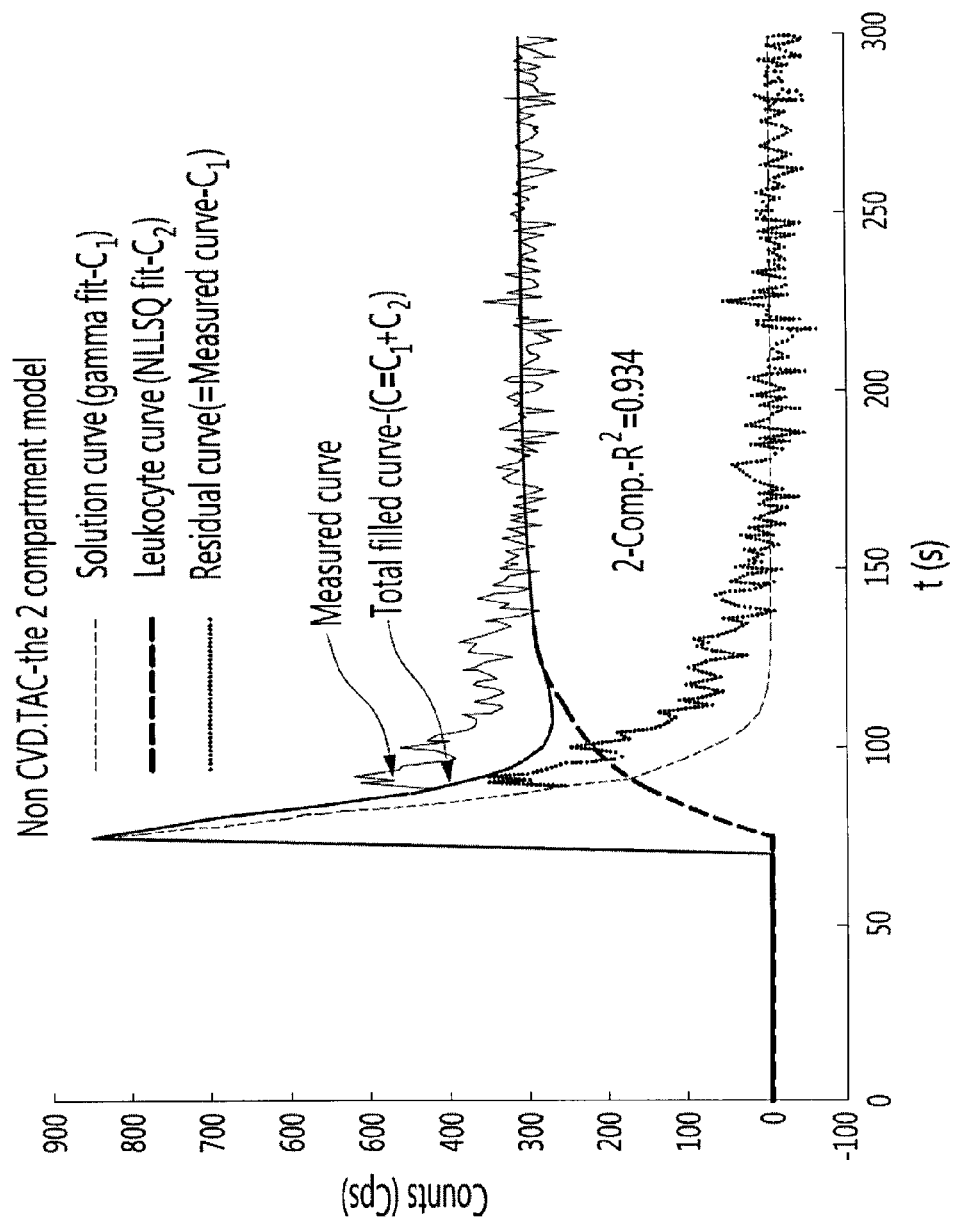
FIG. 2 illustrates time activity curves for a subject without cardiovascular disease generated according to a 2-compartment model indicative of mitochondrial competence. Note that $R^2$ shows a good fit for the model. TAC=Time Activity Curve. NLLSQ=Nonlinear Least Square.

To circumvent this problem, in one embodiment of the invention the dynamic time activity curve representing the presence of the labeled compound in a target of interest over time is decomposed into volume of solution and leukocyte sample compartments represented by $c_1$ and $c_2$ as shown in FIG. 2. In the actual curve, the latter segment of the curve seems gradually stable which is thought to represent a cellular uptake compartment $c_2$.

Figure 3:
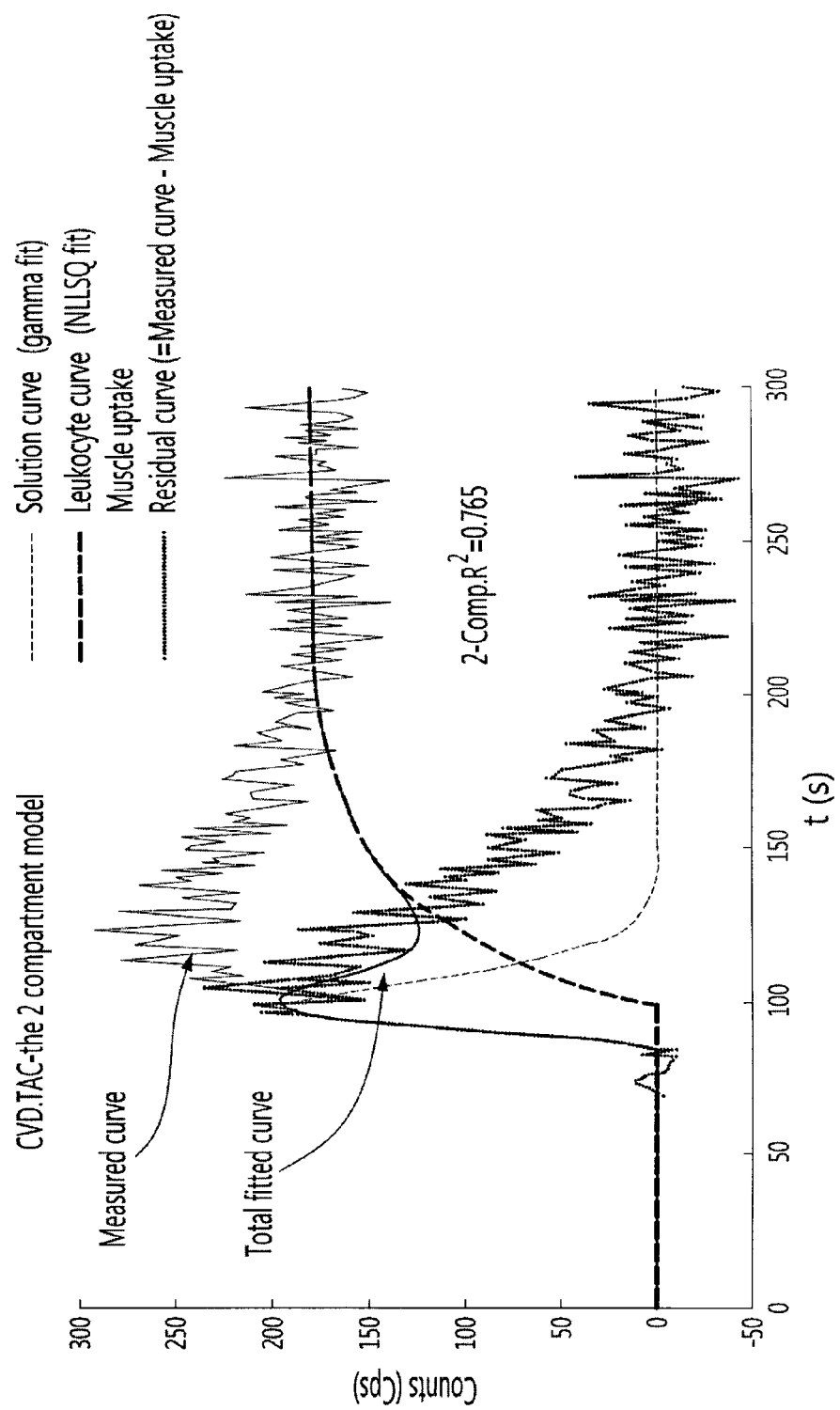
FIG. 3 illustrates time activity curves for a subject with cardiovascular disease generated according to a 2-compartment model indicative of mitochondrial competence.

FIG. 3 provides an example of curves generated using a 3 compartment model to include an input compartment, a mitochondrial uptake compartment and a fitted interstitial space compartment. The 3-compartment model provides a good fit in both patients with (FIG. 6, $R^2=0.974$) and without (FIG. 5, $R^2=0.984$) cardiovascular disease. It is noted that given the good fit of the model in both population groups, the 3-compartment model would likely provide a good model for use in a general population. The "Mitochondrial uptake" curve is thought to reflect the uptake of Tc-99m into the mitochondria in the cells or tissue sample. The fitted interstitial space curve is believed to relate to the presence of label compound in the interstitial or cytosolic space. The "Total fitted curve" is the sum of curves $c_1(t)$, $c_2(t)$ and $c_3(3)$, and is compared to the "Measured curve" obtained from the scintigraph.

The labeled compound $^{99m}$Tc-tetrofosmin is known to be retained by the mitochondria of muscle cells by a mechanism which is dependent on the mitochondrial membrane potential (See Product Monograph, Myoview™, Amersham Health Inc. 2004). The presence of labeled compound in the third space is therefore thought to be indicative of mitochondrial dysfunction. In one embodiment of the invention, data obtained from analyzing this third compartment is used for determining a quantitative measure or diagnosis of metabolic dysfunction. In a further embodiment, the data is used for determining a quantitative measure or diagnosis or mitochondrial dysfunction.

A person skilled in the art will appreciate that different parameters relating to the third compartment may be used in order to provide a quantifiable metric of mitochondrial function. For example, parameters related to the observed peak activity, the maximal rate of rise of activity (upslope) or the integral of the activity-time curves up to the peak activity or to another point are useful in quantifying the observed compartments. Additionally, dimensionless parameters consisting of the ratios of these measures with the parameters derived from blank sample and/or control cells (e.g. with added mitochondrial function inhibitors) or tissue sample(s) may also provide a useful measure of metabolic function. These parameters may then be used to diagnose mitochondrial dysfunction, or mitochondrial related diseases if the parameters vary above or below a certain threshold.

The measure of mitochondrial function herein described by the applicants may be useful in the diagnosis of a number of mitochondrial disorders or disease-related states. Mitochondrial related diseases include cancer, infertility, diabetes, heart diseases, blindness, deafness, kidney disease, liver disease, stroke, migraine as well as neurodegenerative diseases such as Parkinson and Alzheimer disease. Mitochondrial dysfunction is also related to the toxicity of HIV and other drugs and is involved in aging. Furthermore, the measure of mitochondrial function may also be useful to provide a non-specific indicator of the state of the basic energetic machinery of the cell and be a marker of disease severity or resistance to a treatment that would appeal to a degree of autonomous energy generation. Also, it is thought that the measure of mitochondrial function, when estimated with colloid labelled compounds (e.g. $^{99m}$Tcstannous colloid) could also measure the capacity of leukocytes to incorporate and retain particles of the labeled compound (phagocytose) and estimate the capacity of a subject to fight a disease or infection.

Insulin resistance is a physiological condition where the natural hormone, insulin, becomes less effective at lowering blood sugars. The resulting increase in blood glucose may raise levels outside the normal range and cause adverse health effects. The measure of mitochondrial function may also be used to detect and qualitatively or quantitatively measure the presence or absence or insulin resistance. Any factor having an influence on the basal metabolism is susceptible of influencing insulin resistance. It is believed that the capacity of mitochondria to respond to these factors is an indication of a more general health state of the cells and/or tissue. The build-up or accumulation of lactic acid in cells of diabetic patients intoxicates the mitochondria and negatively influences basal metabolism. Insulin resistance is capable of influencing mitochondrial dysfunction through inadequate insulin signalling, and through the loss of adequate endothelial cell wall dysfunction, both of which have a direct impact on the normal entry of glucose in the cell. Inadequate entry of glucose impairs the activity of the mitochondria.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation. The present invention will be more readily understood by referring to the following examples which are given to illustrate the invention rather than to limit its scope.

Example 1

Quantitative Modeling of Mitochondrial Function Test

The use of 2 and 3-compartment quantitative models as shown in FIG. 2, is examined to analyze the kinetics of the concentration of the labeled compound in a leukocyte sample. In the 2-compartment model, $c_1(t)$ is loosely considered as Tc-99m concentration in the volume of solution represented by the solution time activity curve, and $c_2(t)$ is the concentration in the leukocyte sample. In the 3-compartment model, $c_1(t)$ is the once again considered to represent the volume of solution, $c_3(t)$ is considered mainly as the concentration in the mitochondria, and $c_2(t)$ probably represents the interstitial space or the cytosol. The $k_{ij}$ (i,j=0~3) constants are defined as the rate constants from pool i to j.

Example 2

Sample Processing Through a Measurement Apparatus

Figure 4:
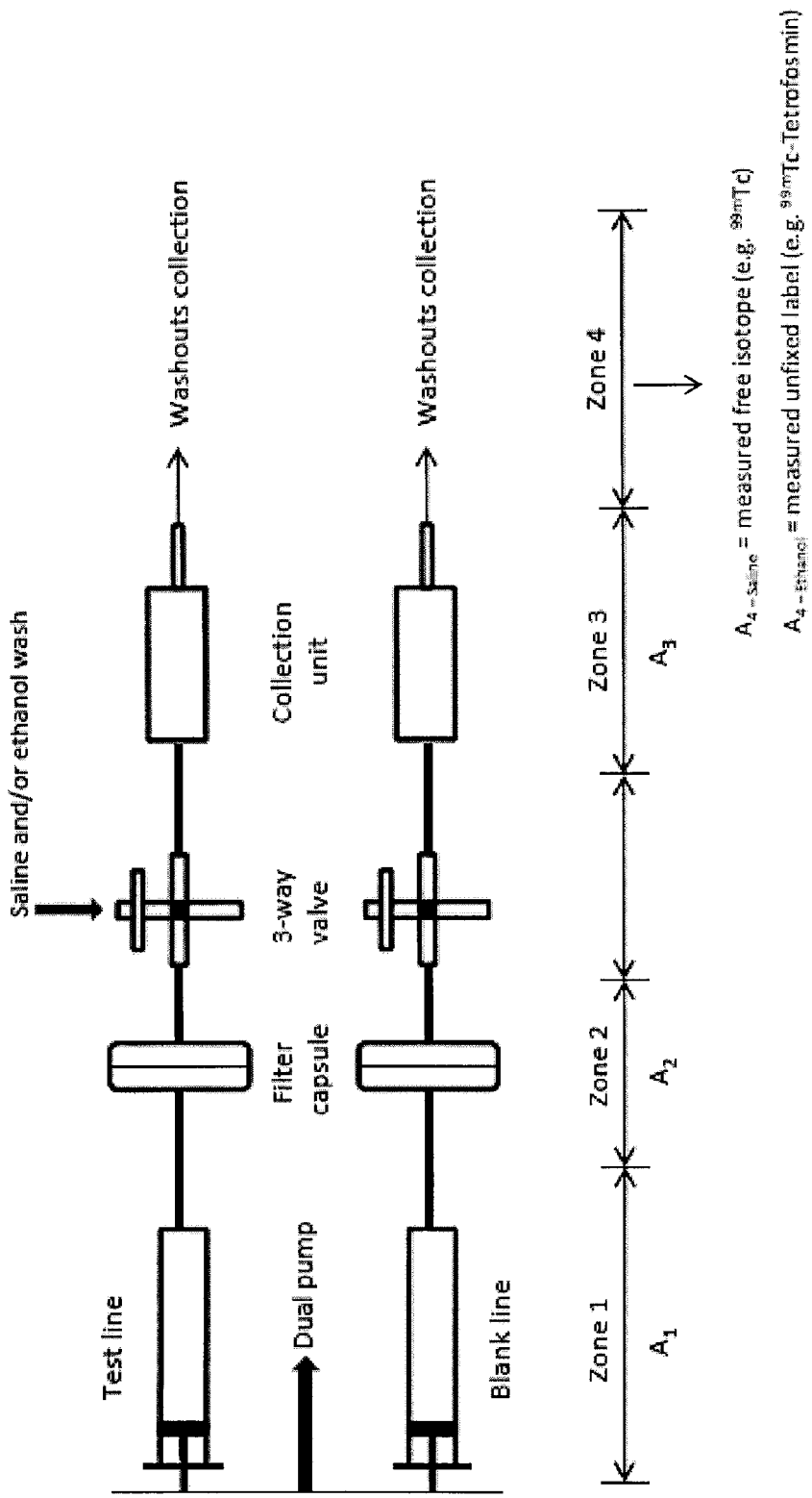
FIG. 4 illustrates a diagrammatic representation of a test setup for measuring labeled compound incorporation in a leukocyte sample according to the present invention.

Now referring to FIG. 4, a leukocyte sample is collected from the blood of a subject The leukocyte sample is placed within a filter capsule capable of retaining the leukocyte sample and being permeable to suitable solutions and the free labeled compound that is added and slowly pushed through the leukocyte sample enabling uptake and reduction by the mitochondrial activity of the said leukocytes. The preparation in then slowly washed with saline, the reduced portion of the labeled compound being retained by the leukocytes whilst the unlabeled will be eluted and collected in the washout compartment or device. The filter capsule is connected to a 3way valve, which is connected to a collection unit capable of capturing the fluid exiting from the filter capsule after introduction of the volume of solution over the labeled leukocyte sample. The collection unit comprises an exit hole from which eluates may be collected. A second "control" line identical to the above described line, but comprising a blank radioactive sample having no leukocyte sample or a cell sample whose mitochondrial activity has been blocked by addition of a specific mitochondrial inhibitor molecule, is assembled in parallel.

A volume of labeled compound (e.g. $^{99m}$Tc-tetrofosmin) is introduced into each filter capsule simultaneously, for example by use of a dual action pump, and the volume of labeled compound thereby introduced flows over the leukocyte sample or the empty filter, to mark the leukocyte sample (or not). A measurement of the total labeled compound in the leukocyte sample is then taken. Next a volume of solution is introduced and flows over the marked leukocyte sample (or the blank sample filter). Any labeled compound which is not incorporated in the mitochondria is washed away by the volume of solution and is collected in the collection unit. A measurement of the labeled compound in the collection unit may be performed to represent a measure of the unincorporated labeled compound, or alternatively, a volume of saline solution may be introduced through the 3way valve to wash the labeled compound captured within the collection unit and be collected from the exit hole. A second ethanol wash may also be introduced and collected. Measurement of the collection unit, and the saline and ethanol wash may then be taken.

Example 3

Fixed Measurements

For measuring the labeled compound in each of predetermined experimental zones, fixed measurement may be made before and after the introduction and passage of the volume of solution over the sample of leukocytes. For example, a fixed measurement of the initial amount of labeled compound ($A_1$) in the total leukocyte sample is made at the beginning (see FIG. 4 zone 1), and after passage of the solution, the amount of labeled compound remaining (or retained) in the leukocyte sample ($A_2$) and in the volume of solution having passed through the filter is measured as the total of the labeled compound retained in the collection unit ($A_3$). Alternatively, the collection unit may be washed with saline and ethanol and the amount of labeled compound present in the saline wash ($A_{4\text{-}saline}$) and ethanol wash ($A_{4\text{ethanol}}$) may be measured. The washes are respectively representative of the free isotope (e.g. free $^{99m}$Tc) and the free labeled compound not fixed by the mitochondria [e.g. unfixed $^{99m}$Tc-tetrofosmin (Myoview™)] soluble in the washes of the volume of solution collected in the collection unit. A measurement of the collection unit is also taken after the washes, and the sum of these measurements ($\Sigma A_3 + A_{4\text{-}saline} + A_{4\text{-}ethanol}$) represents the total amount of unincorporated labeled compound. The value representing the quantity of incorporated labeled compound marking the mitochondria may be calculated by obtaining a ratio of the incorporated versus the unincorporated labeled compound:

$$\frac{(A1 - A2)}{\Sigma((A3) + (A4 - \text{saline}) + (A4 - \text{ethanol}))}$$

Figure 5:
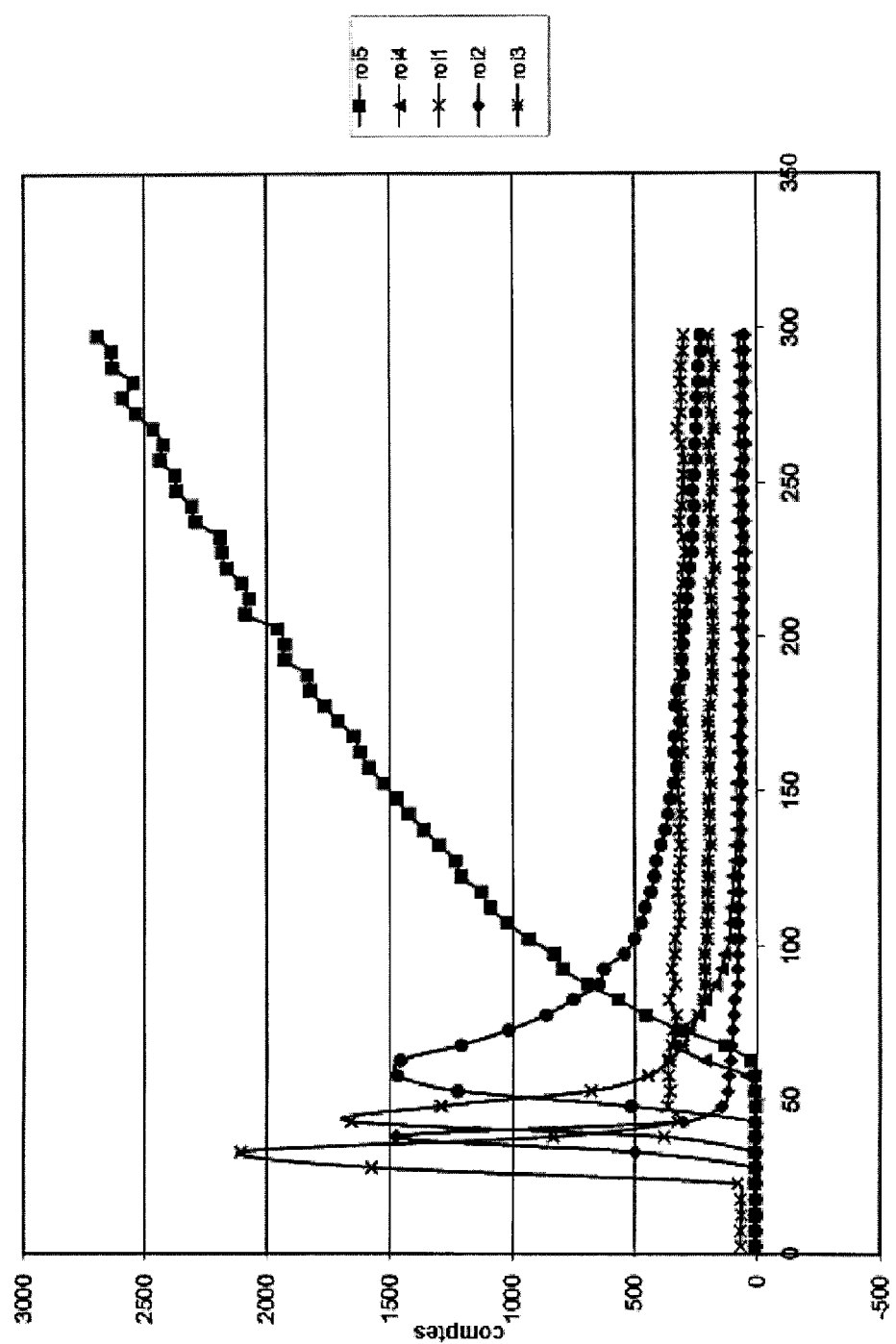
FIG. 5 illustrates time versus radioactive counts for a test setup according to the present invention.

Now referring to FIG. 5, there is presented time versus radioactive measurement curves for the different zones of a test setup according to the present invention. Region of interest 1 (ROI1): zone 2, ROI2: measurement at the 3-way valve, ROI3: measurement out of the 3-way valve, but before the collection unit (seppak), SEPPAK: zone 3, ROI4: measurement out of the seppak, and ROI5: total collected eluate.

Example 4

Kinetic Modeling of Measurements

The presence of the labeled compound may also be measured over time, to record rates of accumulation of the suitable labeled compound in the different zones of the apparatus carrying out the analysis. The speed of the increase in accumulation of the labeled compound in the zone is recorded simultaneously in real time in both a test sample (the test sample of leukocytes) and in a blank sample (comprising all the zones, but excluding or not a leukocyte sample, as explained above). The time-course data of labeled compound is then modeled using a quantitative kinetic modeling techniques to include a component indicative of mitochondrial function. Ratios of the test data versus the blank samples are used, as appropriate. In one embodiment, the time course data is modeled into 3 or more compartments representing the volume of suitable solution uptake of the labeled compound, the uptake into the mitochondria, as well as a compartment thought to represent the presence of the labeled compound in the released fluid after passage over the leukocyte sample.

Figure 6A:
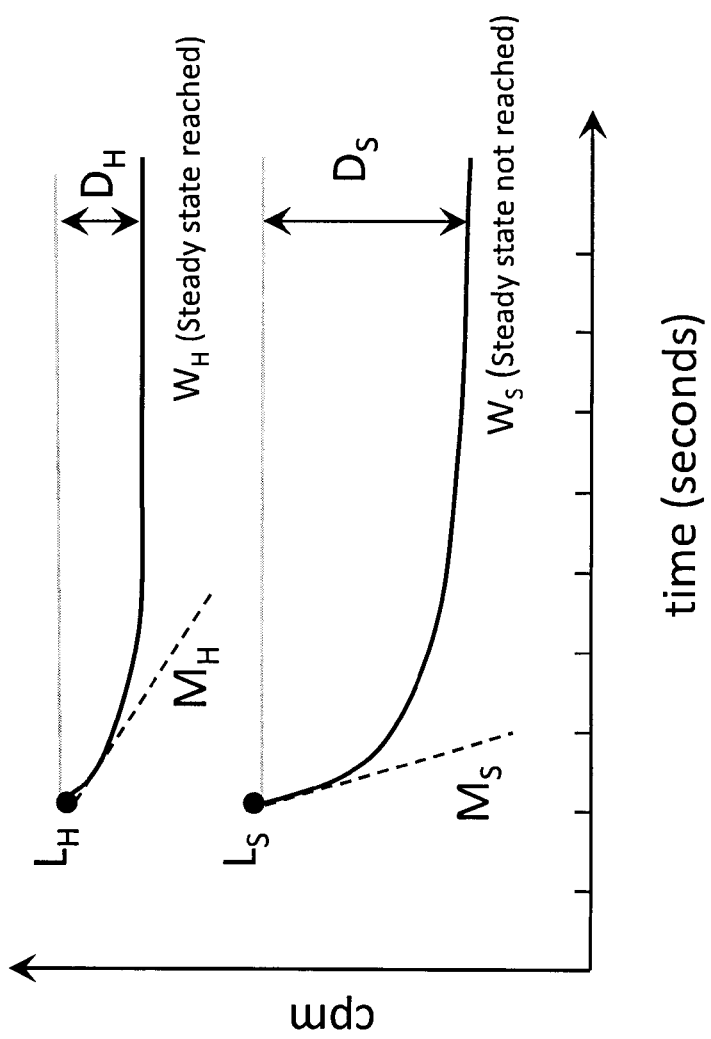
FIG. 6A shows the radioactivity in the viable cell sample while FIG. 6B show radioactivity in the wash solution.

FIG. 6A is a graph showing radioactivity (cpm or counts per minute) as a function of time (in seconds) in an in vitro experiment using leukocytes isolated from blood of healthy (H) and sick (S) donors. The bold line represents the cpm values as a function of time, the dotted line represents the initial rate of decrease in cpm. It will be appreciated that leukocytes can be isolated from a plasma portion of blood by filtration through a filter such as that used in some embodiments of the present invention. Leukocytes can be separated from red blood cells by techniques known in the art such as flow cytometry. Isolating the leukocyte portion of the blood from all other blood cells is, however, not necessary because leukocytes are the main type of mitochondria-containing blood cells. Red blood cells, which are the most abundant cell type in blood, do not typically contain mitochondria.

In FIG. 6A, the "L" value is the initial specific labeling of the sample detected after incubation with the labelling compound and subsequent wash to remove labelling compound that has not been retained by the cells of the sample.

It will be understood by those skilled in the art that the initial specific labeling comprises some labelled compound that have already been reduced by the mitochondria and some labelled compound that is inside the cell but not reduced by the mitochondria. L therefore represents the initial specific labeled compound retained by the cell that has not been eluted with a preliminary wash after the initial labelling period. Initial specific labeling (L), as a standalone value, can be used to determine mitochondrial function/efficiency. The L value is informative with respect to mitochondrial function/efficiency because accumulation of labelled compounds inside the cell occurs at varying rates and starts to accumulate during the initial labelling period. Furthermore the duration of the initial incubation will have an important effect on the slope (M) and the difference between the initial labelling (L) and the steady state labelling (D) detected.

In some cases, a control with no sample can be used as a measure of non-specific labelling and is subtracted from the L value. M represents the slope of initial decrease in label detection (the rate of decrease of labelled compound in the cell sample). D represents the difference between initial specific labelling (L) and the steady state labelling detected. W represents whether a steady state (SS) has been reached after a predetermined duration. It will be understood that radioactivity count can be performed in the sample or it can be indirectly determined by subtracting the cpm in the eluate from the total specifically labelled cpm (L). "W" is a kinetic parameter that represents whether or not a steady state has been attained in a predetermined duration.

Figure 6B:
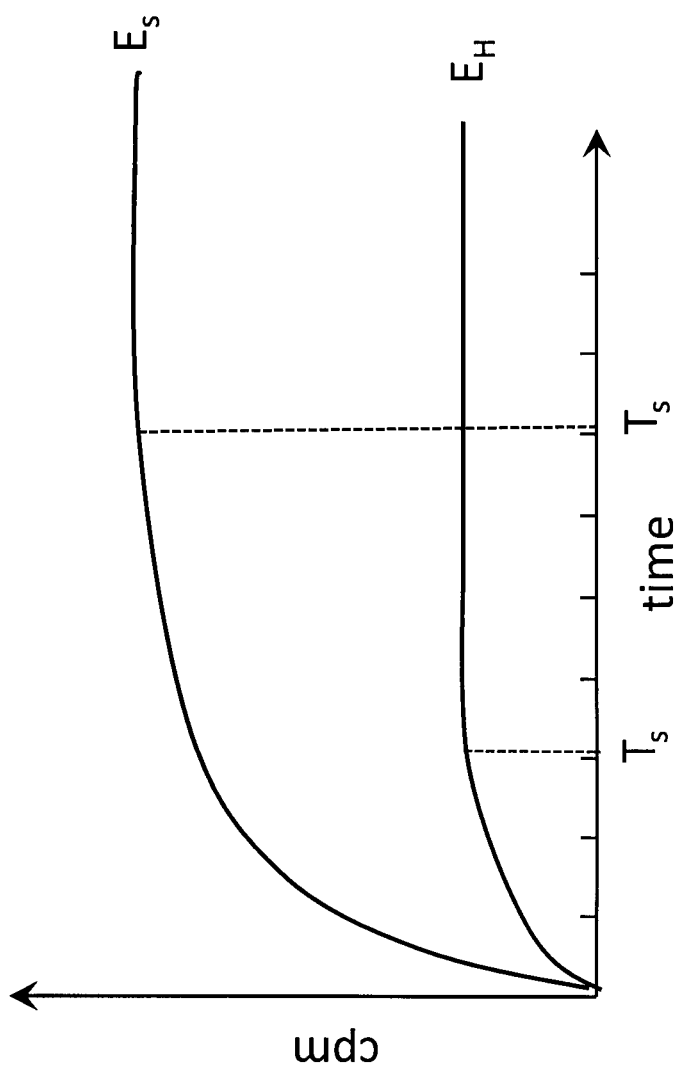
FIG. 6 illustrates graphs of radioactivity (cpm or counts per minute) as a function of time (in seconds) in an in vitro experiment using leukocytes isolated from blood of healthy (H) and sick (S) donors.

FIG. 6B shows a graph similar to that found in FIG. 6A where the difference is that radioactivity is detected in the washing solution (eluate) rather than in the cell sample. In this case, the detected radioactivity is summed and plotted as a function of time to define kinetic parameter "E". Finally "T" represents the duration (e.g. time in seconds) required to attain a steady state value where steady state is defined as an amount of labelled compound detection that is unchanging in a predetermined amount of time, in other words, when the labelled compound has reached a plateau. It can be seen in FIG. 6A that the steady state is not reached for the Sick subject (S) whereas it is reached for the Healthy subject (H). In FIG. 6B, the steady state is attained for both subjects, although significantly faster for the healthy subject.

The rate of "reduction" of labelled compound by mitochondria is a good measure of the efficiency or function of mitochondria and will affect the above mentioned L, M, D, W, E and T kinetic parameters.

In some embodiments, leukocytes do not need to be isolated from blood in order to perform the methods of the present invention because most contaminating cells are red blood cells which, although they increase the non-specific labelling, they do not have mitochondria and therefore do not affect specific labeling. In other embodiments, leukocytes can be isolated from other blood cells by methods known in the art such as, but not limited to, flow cytometry using leukocyte specific markers or centrifugation in a Ficoll gradient It will be appreciated by those skilled in the art that although the mitochondrial activity of leukocytes can be used as a marker for diseases not directly related to the leukocyte itself, the methods of the present invention are also useful for identifying diseases directly involving leukocytes and/or the immune system in general such as, but not limited to, inflammation, autoimmune diseases, allergies and asthma, immune-deficiencies, A viable cell should be understood as being a living cell whose mitochondria are able to reduce a labelled compound of interest according to the present invention. A leukocyte should be understood as being synonymous with white blood cell.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. An in vitro method for determining mitochondrial function of a subject comprising:
providing an apparatus comprising two sample lines, each one of said sample lines comprising a pump, a filter capsule in fluid communication with said pump and positioned downstream from said pump, a collection unit in fluid communication with said filter capsule and positioned downstream from said filter capsule, a first zone associated with said pump, a second zone associated with said filter capsule, and a third zone associated with said collection unit;
providing viable cells or tissue sample isolated from said subject in said filter capsule of a first one of said sample lines, and a blank or reference sample in said filter capsule of the second one of said sample lines;
for each one of said sample lines:
providing in said first zone a solution containing a compound labelled by a radioactive marker and reducible by mitochondria, and introducing from said pump said solution into said sample line and over said sample, thereby exposing said sample to said labelled compound over a labelling period, said labelled compound introduced over said viable cells or tissue sample being reduced by mitochondria of said viable cells or tissue sample to cause a change in a retention of said labelled compound inside said viable cells or tissue sample;
after said labelling period, washing said sample to remove said labelled compound that is released from said sample and produce an eluent collected in said collection unit; and
measuring said levels of said labelled compound in a plurality of: said first zone after said providing in said first zone a solution but before said introducing said solution; said second zone after said washing; and said third zone after said washing, using a scintillation camera; and
determining a level of said mitochondrial function by comparing said levels of said labelled compound measured from said sample lines.

2. The method of claim 1, wherein said viable cells are blood cells.

3. The method of claim 1, wherein said radioactive marker is chosen from $^{99m}$Tc-sestamibi, $^{99m}$Tc-stannous colloid, $^{99m}$Tc-hexamethyhpropylene amine oxime (HMPAO), $^{99m}$Tc-ethylenedicysteine-deoxyglucose, $^{99m}$Tc-tetrofosmin, $^{201}$Thalium-chloride, $^{62}$Cu-glyoxal bis(N4-methylthiosemicarbazone), $^{62}$Cu glyoxal bis(N4-dimethylthiosemicarbazone), $^{62}$Cu-ethylglyoxal bis(N4-methylthiosemicarbazone), $^{62}$Cu-ethylglyoxal bis(N4-ethylthiosemicarbazone), $^{62}$Cu-pyruvaldehyde bis(N4-methylthiosemicarbazone), $^{62}$Cu-pyruvaldehyde bis(N4-dimethylthiosemicarbazone), $^{62}$Cu-pyruvaldehyde bis(N4-ethylthiosemicarbazone), $^{62}$Cu-diacetyl bis(N4-methylthiosemicarbazone), $^{62}$Cu-diacetyl bis(N4-dimethylthiosemicarbazone), $^{62}$Cu-diacetyl bis(N4-ethylthiosemicarbazone), $^{62}$Cu-disalicylaldehyde-1,3-propanediamine, $^{62}$Cu-disalicylaldehyde-2,2-dimethyl-1, 3-propanediamine, $^{62}$Cu-di-4-methoxysalicylaldehyde-1,3-propanediamine, $^{62}$Cu-di-4-methoxysalicylaldehyde-2,2-dimethyl-1,3-propanediamine, $^{62}$Cu-diacetylacetone ethylenediamine, and $^{62}$Cu-diacetylacetone-1,2-propanediamine.

4. The method of claim 3, wherein said radioactive marker is $^{99m}$Tc-tetrofosmin.

5. The method of claim 1, wherein said viable cells or tissue sample is from a bone marrow.

6. The method of claim 1 wherein said measuring said levels of said labelled compound is performed as a function of time to provide time-dependent levels of said labelled compound.

7. The method of claim 6 wherein said determining said level of mitochondrial function further comprises providing a quantitative dynamic multi-compartments model to analyze said time dependent levels of said labelled compound in one or more of said zones to calculate the value of a kinetic parameter indicative of said level of mitochondrial function.

8. The method of claim 1 wherein said labelled compound is selected from nicotinamide adenine dinucleotide (NAD), flavin adenine dinucleotide (FAD), flavin mononucleotide (FMN) and ubiquinone which is reduced by mitochondria of said sample to cause a change in a retention of said labelled compound inside said viable cells or tissue sample.

9. The method of claim 7 wherein said kinetic parameter is the initial rate of decrease of said labelled compound in said viable cells or tissue sample.

10. The method of claim 9, wherein said kinetic parameter is a difference between said labelled compound initially retained by said viable cells or tissue sample following said washing and said labelled compound retained by said viable cells or tissue sample once a plateau is reached with respect to compound retention.

11. The method of claim 7, wherein said quantitative dynamic multi-compartments model includes at least 3 compartments, wherein one of said compartments is indicative of said level of mitochondrial function.

12. The method of claim 1, wherein said reference sample is from one of a normal subject or a diseased subject.

* * * * *